United States Patent
Krishnan et al.

(10) Patent No.: US 10,004,698 B2
(45) Date of Patent: Jun. 26, 2018

(54) FIBRIN WAFER/DISC AS A BIOLOGICAL CARRIER FOR SUSTAINED DELIVERY OF CURCUMIN

(71) Applicants: Sree Chitra Tirunal Institute for Medical Sciences and Technology, Thiruvananthapuram (IN); Indian Council of Medical Research, New Delhi (IN)

(72) Inventors: Lissy Kalliyana Krishnan, Thiruvananthapuram (IN); Lakshmi Sreedharam Pillai, Thiruvananthapuram (IN)

(73) Assignees: Sree Chitra Tirunal Institute for Medical Sciences and Technology, Thiruvananthapuram (IN); Indian Council of Medical Research, New Delhi (IN)

( * ) Notice: Subject to any disclaimer, the term of this patent is extended or adjusted under 35 U.S.C. 154(b) by 8 days.

(21) Appl. No.: 14/888,185

(22) PCT Filed: May 5, 2014

(86) PCT No.: PCT/IN2014/000300
§ 371 (c)(1),
(2) Date: Oct. 30, 2015

(87) PCT Pub. No.: WO2014/192016
PCT Pub. Date: Dec. 4, 2014

(65) Prior Publication Data
US 2016/0101066 A1    Apr. 14, 2016

(30) Foreign Application Priority Data
May 3, 2013   (IN) ............... 1516/CHE/2013

(51) Int. Cl.
A61K 31/12    (2006.01)
A61K 9/00     (2006.01)
A61K 47/42    (2017.01)
A61K 9/19     (2006.01)
A61K 9/70     (2006.01)

(52) U.S. Cl.
CPC ............ *A61K 31/12* (2013.01); *A61K 9/006* (2013.01); *A61K 9/19* (2013.01); *A61K 9/7007* (2013.01); *A61K 47/42* (2013.01)

(58) Field of Classification Search
CPC ........ A61K 31/12; A61K 47/42; A61K 9/006; A61K 9/19; A61K 9/7007
See application file for complete search history.

(56) References Cited

U.S. PATENT DOCUMENTS

2005/0175665 A1*  8/2005  Hunter ............... A61K 45/06
                                                      424/423
2007/0286881 A1* 12/2007  Burkinshsw ....... A61K 9/0024
                                                      424/422

FOREIGN PATENT DOCUMENTS

IN          187639        6/2002

OTHER PUBLICATIONS

Mei Dai et al. "Chitosan-Alginate Sponge: Preparation and Application in Curcumin Delivery for Dermal Wound Healing in Rat", Journal of Biomedicine and Biotechnology, Hindawi Publishing Corp., Sep. 1, 2009, vol. 2009.

* cited by examiner

*Primary Examiner* — Michael B. Pallay
(74) *Attorney, Agent, or Firm* — The Webb Law Firm

(57) ABSTRACT

Provided herein is a drug delivery system for curcumin comprising fibrinogen, thrombin and curcumin.

10 Claims, No Drawings

FIBRIN WAFER/DISC AS A BIOLOGICAL CARRIER FOR SUSTAINED DELIVERY OF CURCUMIN

CROSS-REFERENCE TO RELATED APPLICATIONS

This application is the United States national phase of International Application No. PCT/IN2014/000300 filed May 5, 2014, and claims priority to Indian Patent Application No. 1516/CHE/2013 filed May 3, 2013, the disclosures of which are hereby incorporated in their entirety by reference.

FIELD OF THE INVENTION

This invention relates to a drug delivery system for curcumin.

This invention further relates to a wafer for use as a biological carrier for sustained delivery of curcumin.

BACKGROUND OF THE INVENTION

Application of phytochemicals as drug molecules is an emerging field of research. In recent years there is growing interest in the use of phytochemicals as chemopreventive and chemotherapeutic agents.

Curcumin is a crystalline compound which has been traditionally used in medicine and cuisine in India. Curcumin (diferuloylmethane) is the major active component of turmeric. It has a low intrinsic toxicity, but a wide range of pharamacological activities including antioxidant, anti-inflammatory, antimicrobial, antiamyloid, and antitumor properties. Extensive research over the last 50 years has indicated that this polyphenol can both prevent and treat cancer. The ability of curcumin to induce apoptosis in cancer cells without cytotoxic effects on healthy cells makes it a potential compound for drug development against cancer. Molecular mechanisms that underlie curcumin's selective toxicity against tumor cells are not clearly understood.

Due to its various medicinal, biological and pharmacological activities, curcumin is high on demand and has high market potential. Its beneficial effects on various disease conditions has been already studied and described worldwide. Evidence has also been presented to suggest that curcumin can suppress tumor initiation, promotion and metastasis. Pharmacologically, curcumin has been found to be safe. Human clinical trials indicated no dose-limiting toxicity when administered at doses up to 10 g/day orally.

All of these studies suggest that curcumin has enormous market potential in the prevention and therapy of cancer.

Nevertheless, widespread clinical application of this relatively efficacious agent in cancer and other diseases has been limited due to poor aqueous solubility, and consequently, minimal systemic bioavailability. Curcumin has been administered to the animals via a variety of routes including topical, systemic, intravenous and oral routes of administration but with poor outcome.

In spite of its promising therapeutic index, the problem of its clinical use is not efficient because the biological activity of curcumin is severely limited due to its poor bio-availability. The reasons for reduced bioavailability within the body could be due to low intrinsic activity, poor absorption, high rate of metabolism, inactivity of metabolic products and/or rapid elimination and clearance from the body.

One of the major observations related to curcumin studies involve the observation of extremely low serum levels. A very recent study by Yang et al. showed that 10 mg/kg of curcumin given intravenously in rats gave a maximum serum curcumin level of 0.36 (0.05 µg/ml), whereas a 50-fold higher curcumin dose administered orally gave only 0.06 (0.01 µg/ml) maximum serum level in rats. An oral curcumin dose of 1 g/kg in rats produced a maximum serum curcumin level of 0.5 µg/ml after 45 min of curcumin dosing. Similarly, in a human clinical trial, 3.6 g of curcumin via oral route was found to produce a plasma curcumin level of 11.1 nmol/l after an hour of dosing.

Some of the possible ways to overcome these problems are being explored recently. Adjuvants, which can block metabolic pathways of curcumin, are one of the major means that are being used to improve its bioavailability. Nanoparticles, liposomes, micelles, and phospholipid complexes are other promising novel formulations, which appear to provide longer circulation, better permeability, and resistance to metabolic processes.

Nanoparticle based drug delivery approaches have been a recent research interest for rendering hydrophobic curcumin dispersible in aqueous media, thus circumventing the pitfalls of poor solubility. Nanoparticle based systems for curcumin delivery is still in its infancy and much progress is warranted in this area. Liposomes are excellent drug delivery systems since they can carry both hydrophilic and hydrophobic molecules. It was found that liposomal vehicle is capable of loading more curcumin into cells than either HSA or aqueous-DMSO, and lymphoma cells showed preferential uptake of curcumin to lymphocytes. Micelles and phospholipids complexes can improve the gastrointestinal absorption of natural drugs, thereby giving higher plasma levels and lower kinetic elimination resulting in improved bioavailability.

Both in vitro and in vivo evaluations of a series of indium and gallium complexes of curcumin derivatives and curcumin have shown that the structural modification and/or complex formation of curcumin with metal ions may yield gallium and indium curcuminoids with potential therapeutic applications. Although many curcumin analogues are found to show improved biological activity over curcumin, specific evaluations of structural analogues and derivatives of curcumin to show improved tissue and plasma distribution are lacking.

Fibrin-antibiotic mixtures were used for assessing the possibility of using a biological carrier for local drug delivery and it was concluded that the antibiotic delivery was seen up to 4 days resulting in a prolonged release of drug. Pluronic tri-block copolymer micelle for the formulation of curcumin has been reported. In vitro release profile demonstrated slower and sustained release of curcumin from Pluronic micelles. The lyophilized form of the formulations exhibited good stability for long-term storage. A polymeric nano formulation of curcumin was reported to increase solubility and bioavailability in carbon tetrachloride induced liver injury in mice.

The University of South Floridas "oral curcumin in patients with hereditary allergy treatment research" has been completed and the compound was found to inhibit nuclear factor-B and the role of starting protein-1, thus inhibiting proteins that cause inflammation and anti-inflammatory substances produced. The research will affect the future of curcumin and promote the application on the market. Japanese companies promote the selling point on the edge of water-soluble curcumin, the compound makes the future of cosmetics and functional products in the field of application has been extended, using a fine-grained and unique technology that dramatically improves the absorption of curcumin. The, American company, Unibar demonstrated its Cur Qnetic curcumin formulation ingredients, the main component of 80% curcumin, vanillin and ginger compound formed, and claimed that the product supplements increase immunity and anti-inflammatory effect and the in vitro and in vivo studies confirmed this.

Therefore, the need exists in the art for an efficient drug delivery system for curcumin which will improve its bioavailability and sustained release.

OBJECTS OF THE INVENTION

It is therefore an object of this invention to propose a drug delivery system of curcumin, which increases the bioavailability of curcumin.

It is a further object of this invention to propose a drug delivery system of curcumin, which improves the sustained release of curcumin.

Another object of this invention is to propose a drug delivery system of curcumin, which has antitumor, anti-angiogenic efficacy.

Yet another object of this invention is to propose a drug delivery system of curcumin, which is non-toxic and biodegradable.

These and other objects and advantages of the invention will be apparent to a person skilled in the art, on reading the ensuing description.

DETAILED DESCRIPTION OF THE INVENTION

According to this invention is provided a drug delivery system for curcumin.

In accordance with this invention, is provided a fibrin based carrier system for the localized delivery of curcumin to increase its bioavailability and sustained release. When Fibrinogen is cryoprecipitated from human plasma, proteins like fibronectin and albumin gets co-precipitated. Out of 100 mg of cryoprecipitated fibrinogen concentrate used for making fibrin glue, 40% could be albumin. Therefore albumin gets incorporated with the fibrin clot easily and because Human Serum Albumin (HSA) gets incorporated into fibrin clot, it is possible to immobilize drugs with fibrin. A biodegradable and biocompatible film disc has been prepared and curcumin has been incorporated into this disc.

a. Preparation of Fibrin Disc Loaded with Curcumin

Different concentrations of Fibrinogen and Thrombin are used to identify the best combination which can retain maximum quantity of curcumin and get a stable form of fibrin wafer/disc. Fibrinogen isolated from human plasma according to the method disclosed in the applicants Indian Patent number 187639 is reconstituted with water and is drawn into a syringe. The second component thrombin purified using ion-exchange chromatography with an activity of ~300 IU is diluted and reconstituted with water. Curcumin in a concentration of 25 to 100 μM is added to thrombin solution and drawn into the other syringe. Both the syringes are loaded onto syringe holder of the fibrin glue applicator system. Using a common plunger, both the components are simultaneously delivered into culture wells. The polymerized fibrin-curcumin is then lyophilized and stored at 4° C. until use. Different effective concentrations of fibrinogen employed are between 1 to 5 mg/disc, and thrombin in 1 to 5 1 U/disc. The integrity and stability of the fibrin clot was compared after incubation with M199 medium provided with 10% FBS and PBS (pH: 7.4). The lyophilized discs re-suspended in culture medium were observed to be stable for 7 days in M199 media. But the same discs were found to be disintegrating in PBS (pH 7.4) after 72 hours. The concentration optimized for further studies is 2 mg/disc fibrinogen, 2.5 IU/disc thrombin and 50 μM/disc curcumin which formed a stable fibrin clot.

The invention will now be explained in greater detail with the help of the following non-limiting examples.

EXAMPLE 1

100 mg of fibrinogen was isolated from human plasma by the method described in Applicant's Indian Patent No. 187639, and reconstituted with 1 ml water and drawn into a syringe. The concentration of fibrinogen employed was such that it could provide an effective concentration of 1 mg/disc. The second component thrombin was purified using ion-exchange chromatography with an activity of ~300 IU, was diluted and reconstituted with 1 ml of water. Curcumin (25 μM concentrations) was added to thrombin solution having a concentration to provide 1 IU/disc and drawn into the other syringe. Both the syringes were loaded onto syringe holder of the fibrin glue applicator system. Using a common plunger, both the components were simultaneously delivered into culture wells. The polymerized fibrin-curcumin was then lyophilized and stored at 4° C. until use.

EXAMPLE 2

100 mg of fibrinogen was isolated from human plasma by the method described in Applicant's Indian Patent No. 187639, and reconstituted with 1 ml water and drawn into a syringe. The concentration of fibrinogen employed was such that it could provide an effective concentration of 2 mg/disc. The second component thrombin was purified using ion-exchange chromatography with an activity of ~300 IU, was diluted and reconstituted with 1 ml of water. Curcumin (50 μM concentrations) was added to thrombin solution having a concentration to provide 2.5 IU/disc and drawn into the other syringe. Both the syringes were loaded onto syringe holder of the fibrin glue applicator system. Using a common plunger, both the components were simultaneously delivered into culture wells. The polymerized fibrin-curcumin was then lyophilized and stored at 4° C. until use.

EXAMPLE 3

100 mg of fibrinogen was isolated from human plasma by the method described in Applicant's Indian Patent No. 187639, and reconstituted with 1 ml water and drawn into a syringe. The concentration of fibrinogen employed was such that it could provide an effective concentration of 5 mg/disc. The second component thrombin was purified using ion-exchange chromatography with an activity of ∞300 IU, was diluted and reconstituted with 1 ml of water. Curcumin (100 μM concentrations) was added to thrombin solution having a concentration to provide 100 IU/disc and drawn into the other syringe. Both the syringes were loaded onto syringe holder of the fibrin glue applicator system. Using a common plunger, both the components were simultaneously delivered into culture wells. The polymerized fibrin-curcumin was then lyophilized and stored at 4° C. until use.

b. Retention of Curcumin in the Lyophilized Wafer/Disc:

The lyophilized discs are incubated with dimethyl sulfoxide (DMSO) overnight and the discs are disintegrated in an ultra-sonicator. The samples were centrifuged to remove the disc debris and the absorbance of the supernatant was estimated at 420 nm (Max absorption of curcumin) in a diode array spectrophotometer. For quantification of the eluted curcumin, a standard curve was prepared from different concentrations of curcumin in DMSO. Almost 100% added curcumin was recovered from fibrin discs into DMSO. Out of 50 µM curcumin incorporated into the disc, 49.2 was extracted from the discs.

2 Release Profile:

The lyophilized discs were incubated with 300 (il M199 medium provided with 10% fetal bovine serum (FBS) and PBS (pH 7.4) in culture wells. The plate was kept at 37° C. incubator. The release profile of curcumin into media was analyzed at predefined intervals of 5 min (for any burst release), 24 h, 48 h, 72 h, 96 h and 120, 144 and 168 hours by measuring the absorbance of the media at 420 nm in a diode array spectrophotometer. For quantification of the eluted curcumin, a standard curve was prepared from different concentrations of curcumin dissolved in water. The release of curcumin into M199 media was stable for 120 h with Fibrinogen 2 mg/disc, Thrombin 2.5 IU and curcumin 50 µM. Out of 50 µM conc of curcumin incorporated, a total of 46.53 µM of curcumin was altogether released in 168 h. But in PBS, the release of curcumin persisted only for 72 hours only even when different combinations of fibrinogen, Thrombin and curcumin were employed, after this period, the wafers/discs disintegrated fully.

3 Analysis of the Effect of Released Curcumin:

Binding of Annexin V to the exposed phosphatidyl serine of mitochondrial membrane and Propidium Iodide to the dead cell nucleus was studied using Alexa Fluor 488 Annexin V/Dead cell Apoptosis kit (Invitrogen-Molecular Probes). Cell cycle analysis was analyzed after staining with PI of the fixed cells after different periods of drug treatment and data was analyzed by Flowjo software.

Briefly, $5 \times 10^5$ cells [A549 (Human Lung Carcinoma) and PC3 (Human Prostate carcinoma)] were seeded in 6 well plates in the appropriate growth media supplemented with 10% FBS and antibiotics. After 24 h, the discs (Fib 2 mg/disc, Thr 2.5 IU/disc and Cur 50 µM/disc) were placed into cell cultures and incubated for 24 h/48 h/72 h to estimate the activity of curcumin at each period. After the treatment period, the cells were harvested and processed for flow cytometric analysis to determine the extent of apoptosis and cell cycle arrest. The differences in morphological features were also analyzed by microscopy. Flow cytometry studies revealed that the fibrin-curcumin wafers/discs induced apoptosis and cell cycle arrest in Lung cancer and Prostate cancer cells in a time and dose dependent manner. The photographs of cells also supported the cell death.

Curcumin mediates its anti-proliferative and apoptotic effects on cancer cells, including cancer stem/progenitor cells and their progenies, through multiple molecular mechanisms. In spite of its promising therapeutic index, clinical use is limited due to its poor solubility in aqueous medium which causes poor bioavailability. This product claims immobilization of curcumin with human fibrin clot which is converted to a lyophilized wafer. Upon suspending the wafer in tissue culture medium, sustained release of curcumin is achieved in an active form without any metabolism of the drug. The release drug demonstrated the ability to arrest the proliferation of human cancer cells and endothelial cells and induced cell death in culture. The use of the drug incorporated fibrin wafer/disc enables availability of the drug in the local milieu in a soluble and effective manner.

We claim:

1. A drug delivery system for curcumin comprising a disc or wafer consisting of curcumin and fibrin, the fibrin being polymerized from fibrinogen and thrombin.

2. The drug delivery system as claimed in claim 1, wherein, prior to polymerization, fibrinogen is present in 1 to 5 mg/disc, thrombin in 1 to 5 IU/disc and curcumin in 25 to 100 µM per disc.

3. The drug delivery system as claimed in claim 1, wherein, prior to polymerization, fibrinogen is present in 2 mg/disc, thrombin in 2.5 IU/disc and curcumin in 50 µM/disc.

4. A process for the preparation of a drug delivery system for curcumin, the drug delivery system comprising a disc or wafer consisting of curcumin and fibrin, the fibrin being polymerized from fibrinogen and thrombin, the method comprising drawing fibrinogen solution into a syringe, adding curcumin to reconstituted purified thrombin solution to obtain a mixture followed by loading a second syringe with the mixture, simultaneously delivering the fibrinogen solution and the curcumin-thrombin mixture into culture wells for polymerization to take place, followed by lyophilisation of the polymerized product to obtain the drug delivery system.

5. The process as claimed in claim 4, wherein fibrinogen is obtained by reconstituting fibrinogen isolated from human plasma.

6. The process as claimed in claim 4, wherein fibrinogen is present in 1 to 5 mg in the solution.

7. The process as claimed in claim 4, wherein thrombin is present in 1 to 5 IU in the mixture.

8. The process as claimed in claim 4, wherein curcumin is present in 25 to 100 µM in the mixture.

9. The drug delivery system as claimed in claim 1, wherein the fibrinogen, thrombin, and curcumin are stable and sterile for more than 7 days in tissue culture medium supplemented with 10% fetal calf serum.

10. The drug delivery system as claimed in claim 1, wherein the drug delivery system demonstrates a sustained release pattern of curcumin for 168 hours (7 days) without causing drug metabolism.

* * * * *